United States Patent [19]
Baker et al.

[11] Patent Number: 5,447,504
[45] Date of Patent: Sep. 5, 1995

[54] MISTING APPARATUS FOR THE TREATMENT OF INJURED AREAS AND METHOD THEREFOR

[76] Inventors: Gregg R. Baker; Linda K. Baker, both of 1972 E. Sunburst, Tempe, Ariz. 85284

[21] Appl. No.: 57,172

[22] Filed: May 3, 1993

[51] Int. Cl.⁶ ............................................. A61M 35/00
[52] U.S. Cl. ..................................... 604/289; 601/166; 602/14; 664/290
[58] Field of Search ................ 604/289, 290; 601/166; 4/615, 621, 622; 602/13, 14

[56] References Cited
U.S. PATENT DOCUMENTS
4,353,359  10/1982  Milbauer .................... 601/166

Primary Examiner—J. L. Kruter
Attorney, Agent, or Firm—Harry M. Weiss

[57] ABSTRACT

A misting apparatus for the treatment of injured areas and method therefor is disclosed having at least a containment portion for enclosing a patient's injured area, a plurality of misters located within the containment portion for atomizing medicinal type fluids for application to the injured area, flushing portion coupled to the containment portion for admitting cleaning fluids to the containment portion, and a drainage portion coupled to the containment portion for removing fluids located within the containment portion.

5 Claims, 3 Drawing Sheets

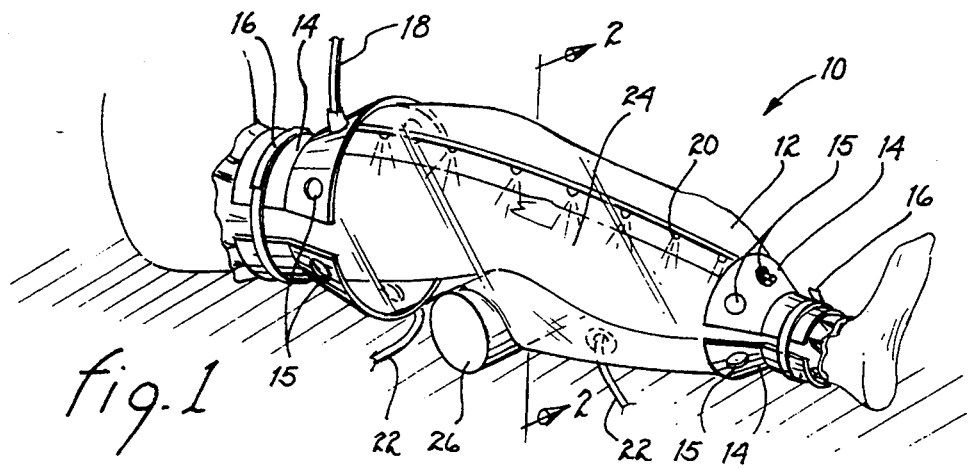
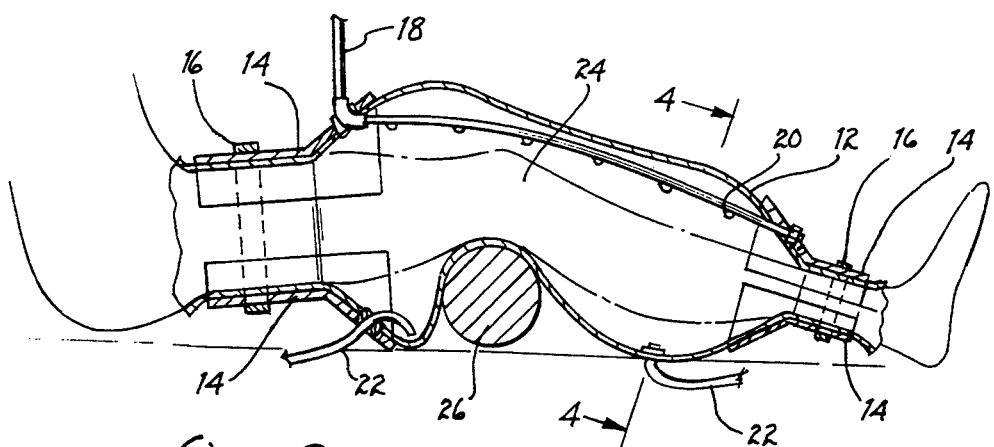
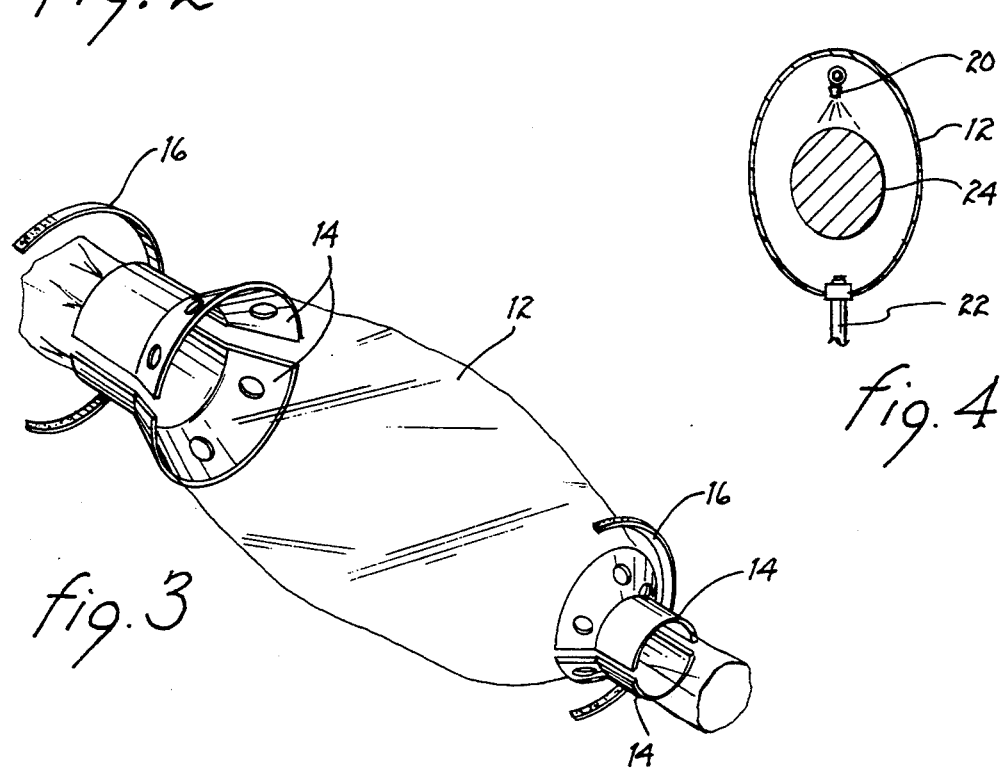
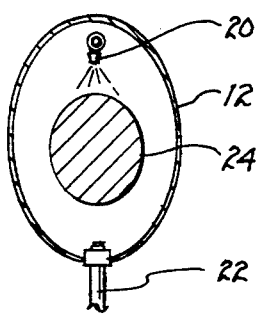

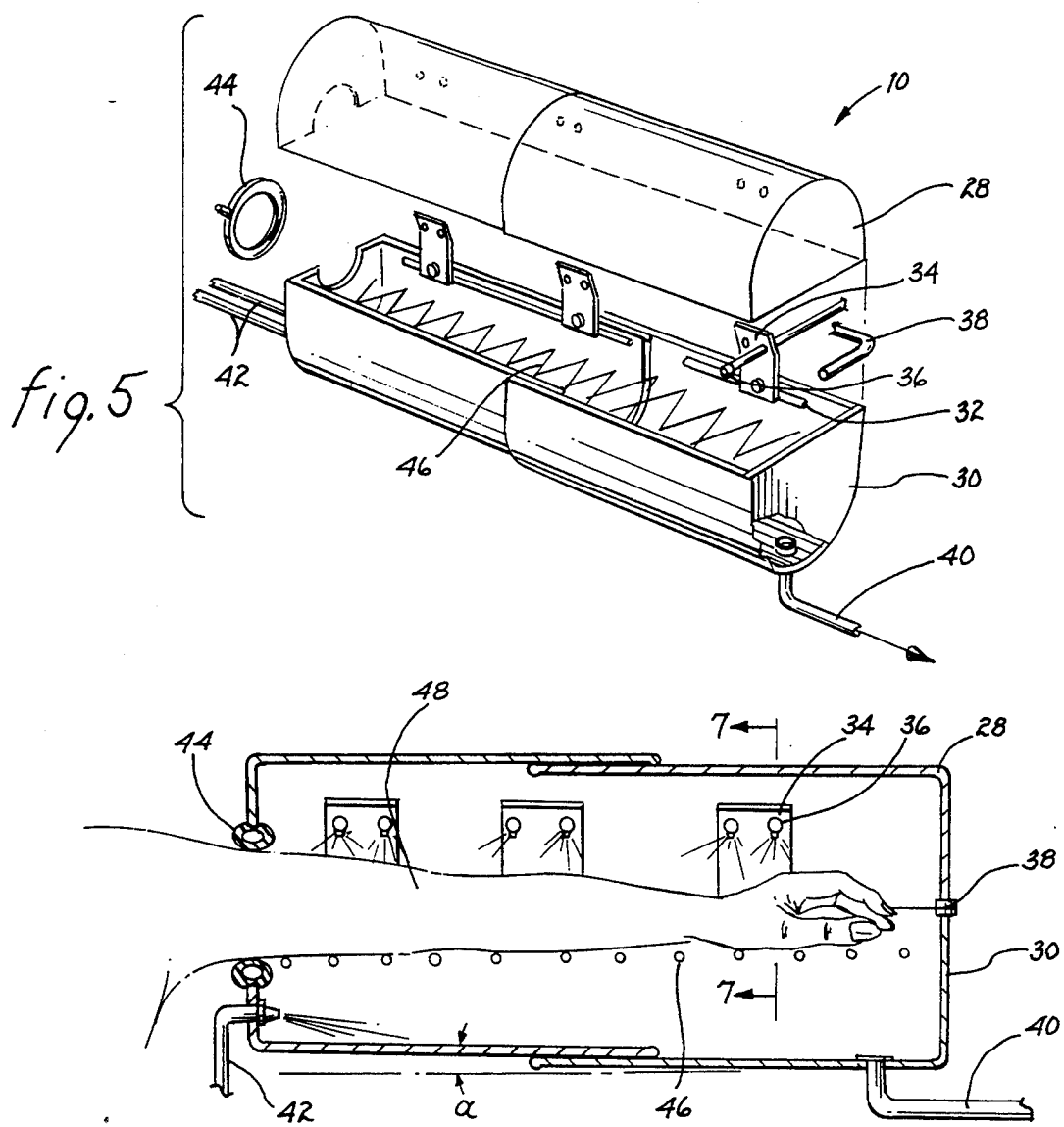

1

MISTING APPARATUS FOR THE TREATMENT OF INJURED AREAS AND METHOD THEREFOR

FIELD OF THE INVENTION

This invention relates generally to medical type devices and, more specifically, to misting apparatus for the treatment of injured areas and methods therefor having at least a containment portion for enclosing a patient's injured area, a plurality of misters located within the containment portion for atomizing medicinal type fluids for application to the injured area, a flushing portion coupled to the containment portion for admitting cleaning fluids to the containment portion, and a drainage portion coupled to the containment portion for removing fluids located within the containment portion.

DESCRIPTION OF THE PRIOR ART

Medical treatments oftentimes require that a portion of a patient's anatomy be kept free from drying out and free from potential sources of contamination. For example, patients undergoing a fasciotomy, an extremity re-attachment, or burn therapy typically require that the area in need of the treatment be covered with gauze or some similar type of material that has been moistened with a medicinal type fluid. The primary problem with this prior art approach to providing these types of medical treatments is that they tend to be extremely painful for the patient. In particular, the injured areas requiring these types of treatments are exceptionally sensitive, open areas. The direct contact of wet gauze on top of an open wound can be very painful. Moreover, the sheer weight of the wet gauze of the prior art treatment tends to cause most patients some discomfort. In addition, as the gauze dries, it must be removed to allow the application of clean, moist gauze. The shortcomings of this gauze type treatment of the prior art can be summarized by at least two disadvantages. The weight of the wet gauze on top of a tender area is extremely painful and, the direct contact of the porous textured surface associated with the gauze literally pulls portions of the injured area when the gauze is periodically removed to allow the application of clean, moist gauze. Therefore, a need existed to create a misting apparatus for the treatment of injured areas that minimizes the exposure of injured areas to contamination and that provides a source of medicinal type fluids without having to directly contact the sensitive injured area.

SUMMARY OF THE INVENTION

In accordance with one embodiment of this invention, it is an object of this invention to provide misting apparatus for the treatment of injured areas and methods therefor.

It is another object of this invention to provide misting apparatus for the treatment of injured areas that atomize at least one of either a warm and a cool medicinal type fluid for reducing the probability of the occurrence of infection and for preventing a patient's injured area from drying out.

It is a further object of this invention to provide misting apparatus for the treatment of injured areas that permit removal of waste materials located within a containment portion without having to open the containment portion and expose the injured area to potential sources of contamination.

BRIEF DESCRIPTION OF THE PREFERRED EMBODIMENTS

In accordance with one embodiment of this invention, a misting apparatus for use in the treatment of an injured area is disclosed comprising, in combination, containment means having a first and a second open end to move the containment means into a position over the injured area of a patient for enclosing the injured area, clamping means coupled to the containment means and having a plurality of clamping portions for removably clamping around portions of the containment means adjacent to each of the first open end and the second open end of the containment means, misting means having a plurality of misters located within the containment means for atomizing at least one of a warm and a cool medicinal type fluid for application to the injured area, and drainage means coupled to the containment means and having at least one drain port for removing the fluid from the containment means. In addition, the clamping means have VELCRO strap means for providing rapid clamping and unclamping around the containment means.

In accordance with another embodiment of this invention, a method of operating a misting apparatus for use in the treatment of an injured area is disclosed comprising the steps of providing containment means having a first and a second open end to move the containment means into a position over the injured area of a patient for enclosing the injured area, providing clamping means coupled to the containment means and having a plurality of clamping portions for removably clamping around portions of the containment means adjacent to each of the first open end and the second open end of the containment means, providing misting means having a plurality of misters located within the containment means for atomizing at least one of a warm and a cool medicinal type fluid for application to the injured area, and providing drainage means coupled to the containment means and having at least one drain port for removing the fluid from the containment means. In addition, this method also includes the step of providing clamping means having VELCRO strap means for affording rapid clamping and unclamping around the containment means.

In accordance with yet another embodiment of this invention, a misting apparatus for use in the treatment of an injured area is disclosed comprising, in combination, containment means having an upper and a lower telescopic member for slideably adjusting a lengthwise portion of at least one of the upper and lower telescopic members for enclosing the injured area wherein the upper and lower telescopic members form an opening at one end of the containment means, inflatable seal means for insertion between a first space located between the upper and lower telescopic members and for sealing a second space located between a circumferential edge portion of the opening and a portion of a patient's anatomy extending through the opening, misting means located within the containment means and having a plurality of misters for atomizing at least one of a warm and a cool medicinal type fluid for application to the injured area, flushing means coupled to the containment means and having at least one port for admitting cleansing type fluids to clean an interior portion of the containment means, and drainage means having at least one drain port for removing fluids located within the containment means. In addition, the containment means has support means located therein for supporting a portion of the patient's anatomy.

In accordance with yet another embodiment of this invention, a method of operating a misting apparatus for use in the treatment of an injured area is disclosed comprising the steps of providing containment means having an upper and a lower telescopic member for slideably adjusting a lengthwise portion of at least one of the upper and lower telescopic members for enclosing the injured area wherein the upper and lower telescopic members form an opening at one end of the containment means, providing inflatable seal means for insertion between a first space located between the upper and lower telescopic members and for sealing a second space located between a circumferential edge portion of the opening and a portion of a patient's anatomy extending through the opening, providing misting means located within the containment means and having a plurality of misters for atomizing at least one of a warm and a cool medicinal type fluid for application to the injured area, providing flushing means coupled to the containment means and having at least one port for admitting cleansing type fluids to clean an interior portion of the containment means, and providing drainage means having at least one drain port for removing fluids located within the containment means. In addition, this method includes the step of providing the containment means having support means located therein for supporting a portion of the patient's anatomy.

In accordance with still another embodiment of this invention, a misting apparatus for use in the treatment of an injured area is disclosed comprising, in combination, containment means having an upper and a lower portion for enclosing the injured area, misting means having a plurality of misters located within the containment means for atomizing at least one of a warm and a cool medicinal type fluid for application to the injured area, flushing means coupled to the containment means and having at least one port for admitting cleansing type fluids to clean an interior portion of the containment means, and drainage means coupled to the containment means and having at least one drain port for removing fluids located within the containment means. In addition, the upper and the lower portion of the containment means are provided with fastening means for removably attaching the upper portion to the lower portion of the containment means.

In accordance with still another embodiment of this invention, a method of operating a misting apparatus for use in the treatment of an injured area is disclosed comprising the steps of providing containment means having an upper and a lower portion for enclosing the injured area, providing misting means having a plurality of misters located within the containment means for atomizing at least one of a warm and a cool medicinal type fluid for application to the injured area, providing flushing means coupled to the containment means and having at least one port for admitting cleansing type fluids to clean an interior portion of the containment means, and providing drainage means coupled to the containment means and having at least one drain port for removing fluids located within the containment means. In addition, this method includes the step of providing the upper and the lower portion of the containment means having fastening means for removably attaching the upper portion to the lower portion of the containment means.

The forgoing and other objects, features, and advantages of the invention will be apparent from the following, more particular, description of the preferred embodiments of the invention, as illustrated in the accompanying drawings.

BRIEF DESCRIPTION OF THE DRAWINGS

FIG. 1 is a perspective view of one possible embodiment of the misting apparatus for use in the treatment of an injured area showing a patient's leg contained by the apparatus and propped up below the knee by a cylindrical support.

FIG. 2 is a side view of the misting apparatus for use in the treatment of an injured area from FIG. 1.

FIG. 3 is an elevational view of the misting apparatus for use in the treatment of an injured area from FIG. 1 showing the open VELCRO straps around the clamping portions.

FIG. 4 is a cross sectional view of the misting apparatus for use in the treatment of an injured area taken along the line 4—4 of FIG. 2 showing one of the plurality of directional misters atomizing a medicinal type fluid and showing one of the plurality of drain connections.

FIG. 5 is a perspective view of another possible embodiment of the misting apparatus for use in the treatment of an injured area.

FIG. 6 is a side view of a patient extending an arm into the misting apparatus for use in the treatment of an injured area from FIG. 5 showing the misters atomizing a fluid for application to the patient's arm and showing the flushing connection while admitting a cleansing type fluid into the apparatus.

FIG. 7 is a cross sectional view of the misting apparatus for use in the treatment of an injured area taken along the line 7—7 of FIG. 6 showing how the misters are held by movably plates.

DESCRIPTION OF THE PREFERRED EMBODIMENT

Figure 8:
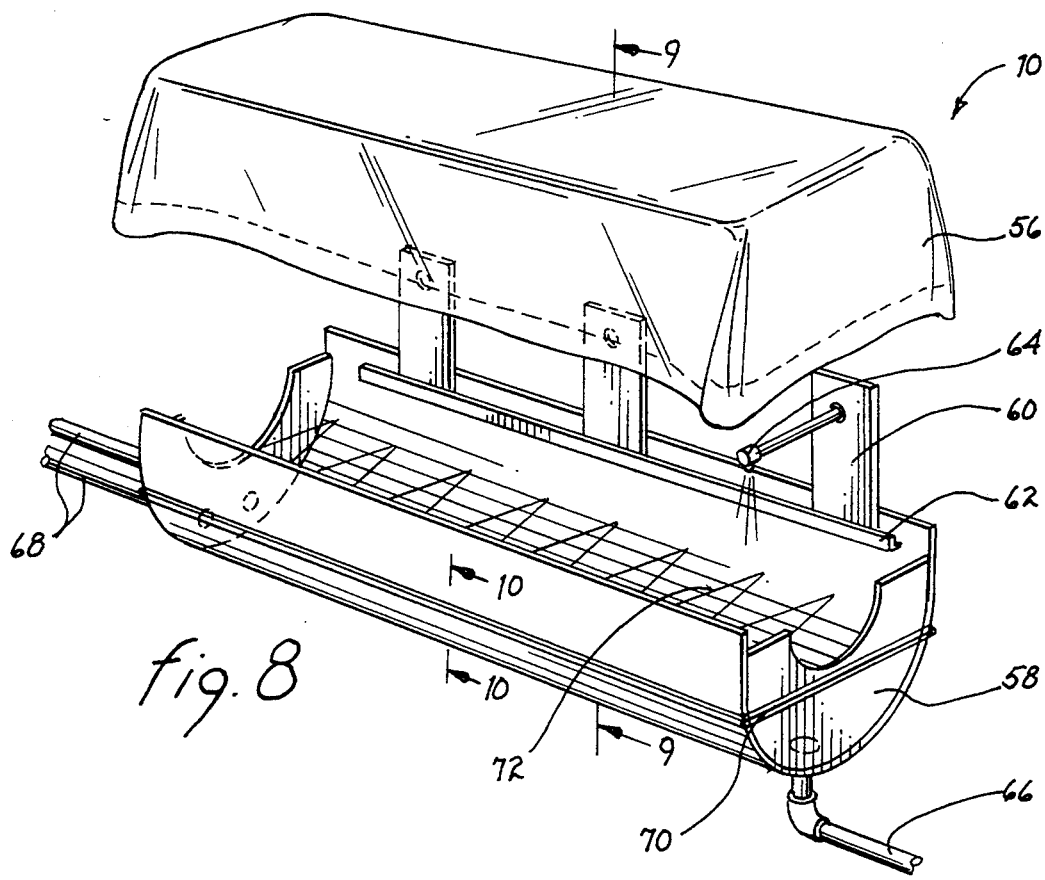
FIG. 8 is perspective view of still another possible embodiment of the misting apparatus for use in the treatment of an injured area.

Referring to FIGS. 1 and 2, one possible embodiment of a misting apparatus for use in the treatment of an injured area is shown and is generally designated by the reference number 10. A container 12 fits over an injured area of a leg 24. The container 12 is substantially transparent, flexible and occlusive. The occlusive feature allows the passage of air from the inside of the container 12 to the outside while simultaneously tending to restrict air passing from the exterior to the interior of the container 12. A plurality of clamps 14 are held around the ends of the container 12 by a plurality of VELCRO straps 16. Hook and loop fasteners which may be used. Medicinal type fluids are delivered at specific temperatures and flow rates through a conduit 18 and subsequently to a plurality of misters 20 for atomizing the fluid for application to an injured area. Note that an external pressure source (not shown) such as a compressed air source provides the necessary driving head to propel the medicinal type fluids through the misters 20. Each of the clamps 14 have a plurality of access ports 15 for supporting the conduits 18, so a plurality of conduits 18 each having a plurality of misters 20 could be implemented in conjunction with the plurality of access ports 15 if desired. A plurality of drains 22 are coupled to the container 12 in order to remove fluids by gravity and/or suction. Also, a support member 26 rests beneath the container 12 in the vicinity of the knee of the leg 24.

Referring to FIG. 3, the clamps 14 are located near the open ends of the container 12 and the VELCRO straps 16 are open. The use of the VELCRO straps 16 allows for both easy removal and application of the clamps 14. It should also be noted that the container 12 may include a fastener to allow easy access to the injured area.

Referring to FIG. 4, one of the misters 20 is shown while atomizing a fluid for application to an injured area of the leg 24. Each of the misters 24, are adjustable in the direction of flow of the fluid.

Referring to FIG. 5, another possible embodiment of the misting apparatus 10 is shown. An upper 28 and lower 30 telescopic member form a containment portion for enclosing a patient's injured area. Either of the upper 28 and lower 30 telescopic members, or perhaps even both members 28 and 30, may be transparent in order to allow a physician to observe the results of the misting treatment without having to open the misting apparatus, thereby exposing the injured area to potential sources of infection. Both the upper 28 and lower 30 telescopic members are adjustable in length in order to accommodate injured areas of different lengths. A plurality of tracks 32 provide the slidable feature of each of the mister plates 34. Each of the plurality of mister plates 34 have a plurality of misters 36 although only one is shown in FIG. 5. A sealing gasket 38 helps seal the edges between the upper 28 and the lower 30 telescopic members. A drain 40 is coupled to the lower telescopic member 30 to remove fluids and/or debris that collects in a portion of the lower telescopic member 30. A plurality of flushing connections 42 are also coupled to the lower telescopic member 30 in order to admit cleansing fluid to flush and clean a portion of the lower telescopic member 30. An opening is formed between the upper 28 and the lower 30 telescopic members of the apparatus 10 for passing an injured area through the opening and into the apparatus 10. An inflatable seal 44 fits around a portion of a patient's anatomy that is passed through the opening at the end of the apparatus 10 for sealing the space between a portion of the patient's anatomy and the circumferential edge formed by the opening. If desired, the upper 28 and the lower 30 telescopic members may have an opening at both ends in order to allow a portion of a patient's anatomy to pass completely through the apparatus 10, and similarly, a second inflatable seal 44 could be used with this second opening. A support structure such as the web support 46 is provided to brace a portion of a patient's anatomy.

Referring to FIG. 6, a patient's arm 48 extends into the misting apparatus 10 while the misters 34 are atomizing a medicinal type fluid for application to an injured portion on the arm 48. In addition, the flushing connections 42 admit a cleansing fluid onto and across a portion of the lower telescopic member 30 to flush stagnant fluids and debris to the drain 40.

Referring to FIG. 7, this cross sectional view taken along line 7—7 of FIG. 6, shows how the mister plates 34 can slide in the tracks 32. The tracks 32 are connected to a portion of the lower telescopic member 30 by connections 52. Moreover, each of the plurality of mister plates 34 have a slide knob 54 for moving the mister plates 34 along the tracks 32. The web support 46 is provided with a plurality of connections 50 for holding up the web support 46 within the apparatus 10.

Figure 9:
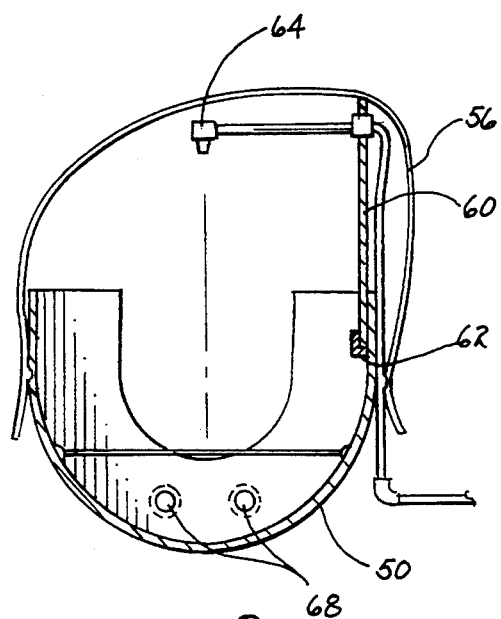
FIG. 9 is a cross sectional view of the misting apparatus for use in the treatment of an injured area taken along the line 9—9 of FIG. 8 showing a mister located within the containment portion.

Referring to FIGS. 8 and 9, yet another embodiment of the misting apparatus 10 is shown. An upper cover 56 is coupled to a lower container 58 via a connection portion 70. A plurality of movable mister plates 60 fit within a track 62 located within the apparatus 10. Each of the plurality of mister plates 60 have at least one mister 64. The lower container 58 also has both a plurality of flushing connections 68 for admitting a cleansing type fluid and at least one drain connection 66 for removing excess fluids from the misting apparatus 10. The misting apparatus 10 also has a support web 72 for holding a portion of a patient's anatomy.

Figure 10:
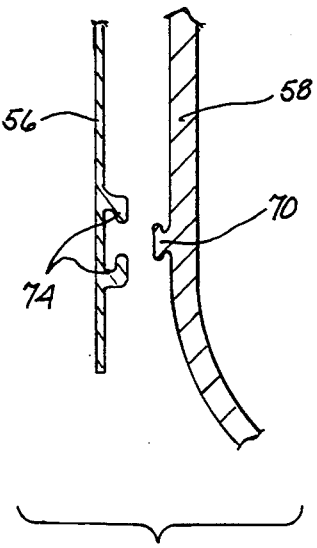
FIG. 10 is a detailed view of the connection between the upper and the lower portions of the misting apparatus enclosure.

Referring to FIG. 10, the arrangement between the connection portion 70 and a portion 74 for receiving the connection portion 70 is shown. This arrangement allows for the quick and easy access into the misting apparatus for accessing the patient's injured area. It should also be noted that the upper cover 56 and/or the lower container may be transparent in order to allow a physician to see the progress of the treatment without having to open the misting apparatus, thereby potentially exposing the injured area to sources of contamination.

OPERATION

Referring to FIGS. 1-4, the container 12 is placed over the patient's injured area. The clamps 14 and the VELCRO straps 16 are then used to enclose the ends of the container 12. The conduit 18 is inserted through two small openings in the container 12 so that it may rest upon the access ports 15. At this stage, medicinal type fluid may be applied to a patient's injured area, and excess fluids are removed from the container 12 via drains 22.

Referring to FIGS. 5-7, the upper 28 and lower 30 telescopic members are placed together along the sealing gasket 38. The inflatable seal 44 is then placed around a portion of a patient's anatomy which is inserted into the apparatus 10 to rest upon the web support 46. The inflatable seal 44 is inflated to seal the space between a portion of the patient's anatomy and the edge of the opening formed by the upper 28 and lower 30 telescopic members. Medicinal type fluids may then be applied to a patient's injured area and excess fluids are removed from the apparatus 10 via the combined action of the flushing connections 42 and the drain 40.

Referring to FIGS. 8-10, the misters 64 are properly aligned using the movable mister plates 60, and a portion of a patient's anatomy is placed into position on the support web 72. Once connection between the upper cover 56 and the lower container 58 is completed, the misting treatment may begin. As previously explained, any excess fluids are removed from the apparatus 10 via the combined action of the flushing connections 68 and the drain 66.

While the invention has been particularly shown and described with reference to the preferred embodiments thereof, it will be understood by those skilled in the art that the foregoing and other changes in form and details may be made therein without departing from the spirit and scope of the invention. For example, although the misting apparatus has been used to treat human patient's, it would be obvious for one skilled in the medical art to use the misting apparatus to treat animals. In addition, since several different features of the different embodiments of the misting apparatus have been defined, it would be obvious for one with reasonable skill in the medical art to combine one or more of these features to create similar misting apparatus.

We claim:

1. A misting apparatus for use in the treatment of an injured area, comprising, in combination:

containment means having a first and a second open end to move said containment means into a position over said injured area of a patient for enclosing said injured area;

clamping means coupled to said containment means and having a plurality of clamping portions for removably clamping around portions of said containment means adjacent to each of said first open end and said second open end of said containment means, said clamping means are provided with a plurality of access ports;

misting means having a plurality of misters located within said containment means for atomizing at least one of a warm and a cool medicinal type fluid for application to said injured area; and drainage means coupled to said containment means and having at least one drain port for removing said fluid from said containment means.

2. The apparatus of claim 1 wherein said containment means is substantially transparent, flexible, and occlusive.

3. The apparatus of claim 1 wherein said clamping means having hook and loop strap means for providing rapid clamping and unclamping around said containment means.

4. The apparatus of claim 1 wherein each of said plurality of misters are adjustable in a direction of flow of said medicinal fluid through said containment means.

5. A method of operating a misting apparatus for use in the treatment of an injured area is disclosed comprising the steps of:

providing containment means having a first and a second open end to move said containment means into a position over said injured area of a patient for enclosing said injured area;

providing clamping means provided with access ports and coupled to said containment means and having a plurality of clamping portions for removably clamping around portions of said containment means adjacent to each of said first open end and said second open end of said containment means;

providing misting means having a plurality of misters located within said containment means for atomizing at least one of a warm and a cool medicinal type fluid for application to said injured area; and providing drainage means coupled to said containment means and having at least one drain port for removing said fluid from said containment means.

* * * * *